(12) United States Patent
Cassell

(10) Patent No.: US 9,844,215 B2
(45) Date of Patent: Dec. 19, 2017

(54) APPARATUSES AND TECHNIQUES FOR SUBTERRANEOUS PLACEMENT OF ONE OR MORE ITEMS

(71) Applicant: Dow AgroSciences LLC, Indianapolis, IN (US)

(72) Inventor: Ronald L. Cassell, New Palestine, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 121 days.

(21) Appl. No.: 13/950,477

(22) Filed: Jul. 25, 2013

(65) Prior Publication Data

US 2014/0033603 A1   Feb. 6, 2014

Related U.S. Application Data

(60) Provisional application No. 61/677,591, filed on Jul. 31, 2012.

(51) Int. Cl.
*A01G 29/00* (2006.01)
*A01M 17/00* (2006.01)
(Continued)

(52) U.S. Cl.
CPC ............ *A01N 25/00* (2013.01); *A01C 5/02* (2013.01); *A01C 15/02* (2013.01); *A01G 29/00* (2013.01); *A01M 17/00* (2013.01); *A01M 21/00* (2013.01); *A01M 21/043* (2013.01); *A01M 25/006* (2013.01); *A01N 25/26* (2013.01); *A01C 7/02* (2013.01)

(58) Field of Classification Search
CPC ...... A01M 7/00; A01M 17/00; A01M 17/002; A01M 21/00; A01M 21/04; A01M 21/043; A01G 7/06; A01G 29/00
USPC ................. 43/124, 131, 132.1; 47/48.5, 57.5
See application file for complete search history.

(56) References Cited

U.S. PATENT DOCUMENTS 1,258,551 A * 3/1918 Fleming .............. A01M 21/043
111/7.2
1,911,692 A * 5/1933 Jalandoni ............... A01C 15/02
111/95
(Continued)

FOREIGN PATENT DOCUMENTS

EP     1599082 B1   10/2007
JP  2005185260 A    7/2005
(Continued)

OTHER PUBLICATIONS

International Search Report dated Dec. 13, 2013 as received in related application No. PCT/US2013/051960.

*Primary Examiner* — David Parsley
(74) *Attorney, Agent, or Firm* — Carl D. Corvin; Maschoff Brennan

(57) ABSTRACT

Apparatuses and techniques for subterranean placement or positioning of one or more items are provided. In one aspect, an apparatus is configured to form a hole in the ground and subsequently provide a pathway for positioning one or more items in the hole. In one form, the items that may subterraneously placed or positioned using the apparatus may include agricultural products such as seeds or delivery vehicles that include one or more fertilizers or pesticides or combinations of these materials.

6 Claims, 8 Drawing Sheets

(51) Int. Cl.
*A01M 21/00* (2006.01)
*A01N 25/00* (2006.01)
*A01N 25/26* (2006.01)
*A01C 15/02* (2006.01)
*A01M 21/04* (2006.01)
*A01M 25/00* (2006.01)
*A01C 5/02* (2006.01)
*A01C 7/02* (2006.01)

(56) References Cited

U.S. PATENT DOCUMENTS

| | | | | |
|---|---|---|---|---|
| 3,170,422 | A | * | 2/1965 | Gregory .................. A01C 5/02 111/96 |
| 3,517,629 | A | | 6/1970 | Bridges et al. |
| 3,771,474 | A | * | 11/1973 | Elston ................. A01M 25/006 111/96 |
| 3,799,081 | A | * | 3/1974 | Wilson .................... A01C 5/02 111/130 |
| 3,815,526 | A | * | 6/1974 | Christopherson ........ A01C 5/02 111/7.2 |
| 4,246,854 | A | * | 1/1981 | Lempa, Jr. ............... A01C 5/02 111/96 |
| 4,413,440 | A | * | 11/1983 | Schultz ............... A01M 25/006 111/95 |
| 4,614,160 | A | * | 9/1986 | Curlett .................... A01C 5/02 111/96 |
| 5,170,729 | A | | 12/1992 | Benner |
| 5,584,256 | A | * | 12/1996 | Fleming .................. A01C 5/02 111/92 |
| 6,502,720 | B2 | * | 1/2003 | Schwederski ....... A01M 25/006 111/96 |
| 2002/0092450 | A1 | | 7/2002 | Sawers |
| 2005/0268829 | A1 | | 12/2005 | Longo |
| 2007/0113924 | A1 | | 5/2007 | Phillips |
| 2010/0297260 | A1 | | 11/2010 | Wilson et al. |

FOREIGN PATENT DOCUMENTS

| | | |
|---|---|---|
| JP | 3124653 U | 8/2006 |
| WO | WO2010126584 A1 | 11/2010 |
| WO | 2011/076773 A1 | 6/2011 |

\* cited by examiner

APPARATUSES AND TECHNIQUES FOR SUBTERRANEOUS PLACEMENT OF ONE OR MORE ITEMS

CROSS-REFERENCE TO RELATED APPLICATIONS

The present application claims priority to U.S. Provisional Patent Application No. 61/677,591 filed Jul. 31, 2012, the content of which is incorporated herein by reference in its entirety.

BACKGROUND

The present application relates to the subterranean placement or positioning of one or more items, and more particularly but not exclusively, to an apparatus configured to form a hole in the ground and subsequently provide a pathway for positioning the one or more items in the hole, and to techniques for using such an apparatus.

Advances in certain areas of technology have given rise to the need for new approaches for the subterranean placement or positioning of certain items. For example, and without limitation, seeds used for agricultural purposes may include an exterior coating or other layer of one or more compositions, including for example pesticide compositions, fertilizer compositions and combinations of the foregoing. In certain instances, individual and selective placement of these and other seeds may be desired in order to avoid, amongst other things, disturbing the exterior coating or other layer. As a further example, delivery vehicles such as capsules which are configured to degrade after their implantation may be used to deliver a desired composition to a field, grove, orchard or other plant growing environment or locus that is in need of treatment by the desired composition. These capsules may release, amongst other possibilities, pesticide compositions, fertilizer compositions and combinations of the foregoing, and may include a structure that is susceptible to breakage or disruption during handling and under current placement techniques which can result in premature release of the composition therefrom. Beyond rendering the capsules unsuitable for their intended function, the premature release of the composition from the capsules may also undesirably expose the handlers thereof to the compositions being released. Accordingly, there is a demand for further improvements in this area of technology.

SUMMARY

Apparatuses and techniques for subterranean placement or positioning of one or more items are provided. In one aspect, an apparatus is configured to form a hole in the ground and subsequently provide a pathway for positioning one or more items in the hole. In one form, the items that may subterraneously placed or positioned using the apparatus may include agricultural products such as seeds or delivery vehicles that include one or more fertilizers or pesticides or combinations of these materials, just to provide a few non-limiting examples.

In one embodiment, an apparatus includes a first member including a first elongate body extending between a proximal end and a distal end. The first elongate body includes an elongate bore and an opening communicating with the elongate bore. The opening is positioned between the proximal and distal ends of the first elongate body. The apparatus also includes a second member including a second elongate body extending between a proximal end and a distal end. The second member is axially movable in the elongate bore of the first member between a first position where the first and second members are axially restrained relative to one another and the distal end of the second member is positioned distally of the distal end of the first member, and a second position where the distal end of the second member is positioned proximally of the opening.

In another embodiment, an apparatus includes a first member including an elongate bore extending therethrough, a second member axially movable in the elongate bore of the first member, and a delivery pathway configured to direct one or more items through at least a portion of the elongate bore for subterranean placement into a hole at least partially formed by a leading tip of the second member extending past an end of the first member.

In yet another embodiment, a method for subterranean placement of at least one item in a hole includes inserting a leading end of an apparatus into ground to form the hole. The apparatus includes an inner member axially movable in an outer member. The method also includes withdrawing the inner member from the hole, and passing the at least one item through the outer member into the hole with at least a portion of the inner member remaining in the outer member.

Other aspects include unique methods, systems, devices, kits, assemblies, equipment, and/or apparatus related to subterranean placement or positioning of one or more items.

Further aspects, embodiments, forms, features, benefits, objects, and advantages shall become apparent from the detailed description and figures provided herewith.

DETAILED DESCRIPTION OF REPRESENTATIVE EMBODIMENTS

Figure 1:
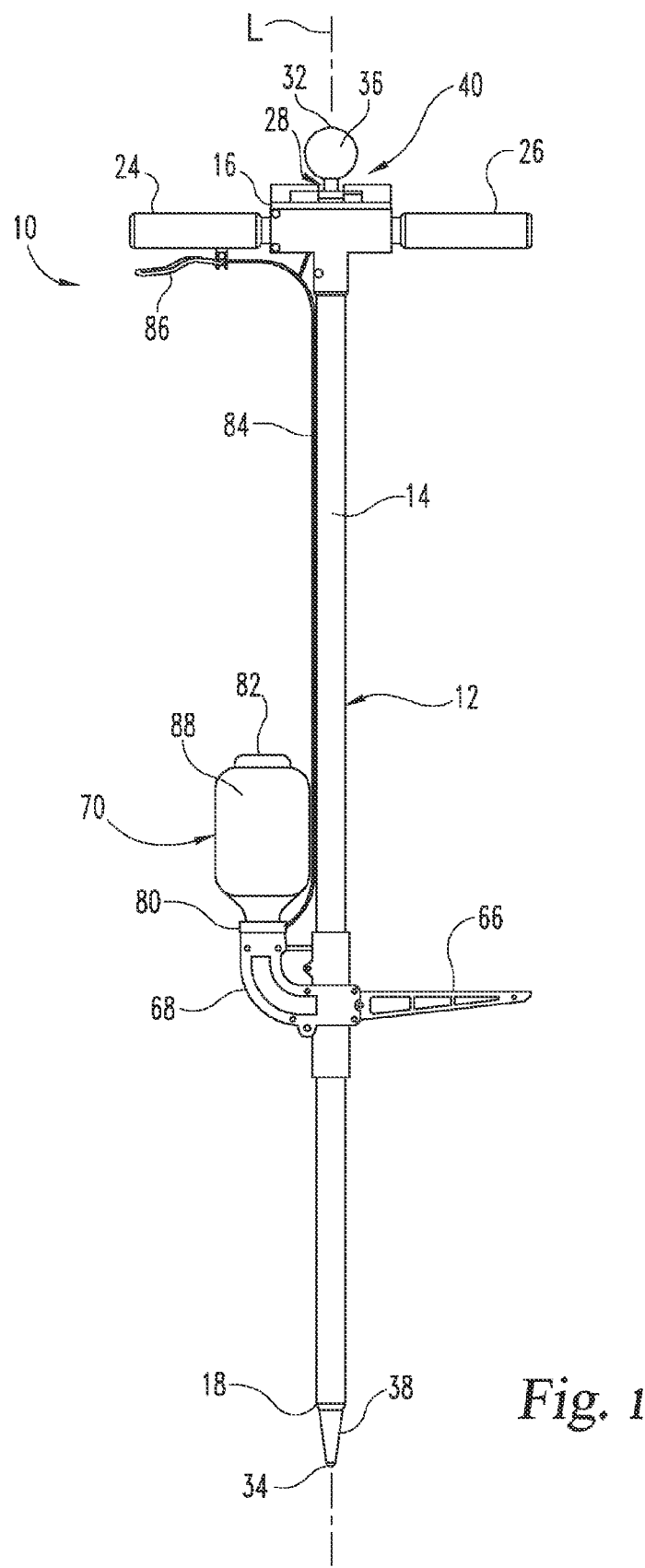
FIG. 1 is a plan view of an apparatus configured for subterranean placement of one or more items.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Systems, devices, apparatuses and techniques for subterranean placement or positioning of one or more items are provided. In one aspect, an apparatus is configured to form a hole in the ground and subsequently provide a pathway for positioning one or more items in the hole. In one form, the items that may subterraneously placed or positioned using the apparatus may include agricultural products such as seeds or delivery vehicles that include one or more fertilizers or pesticides or combinations of these materials, just to provide a few non-limiting examples.

Figure 6:
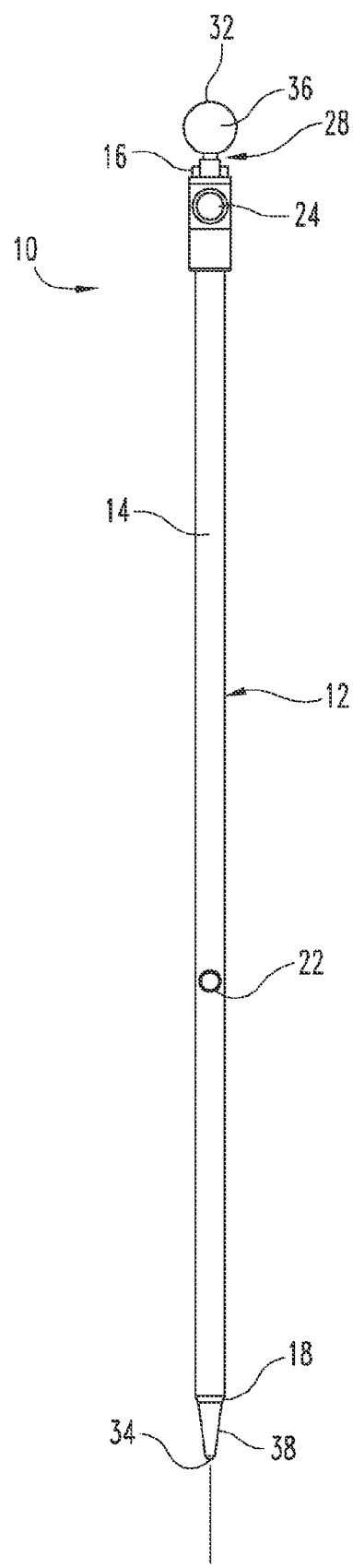
FIG. 6 is an alternative plan view of the apparatus illustrated in FIG. 1 in which some elements illustrated in FIG. 1 have been omitted.
Figure 7A:
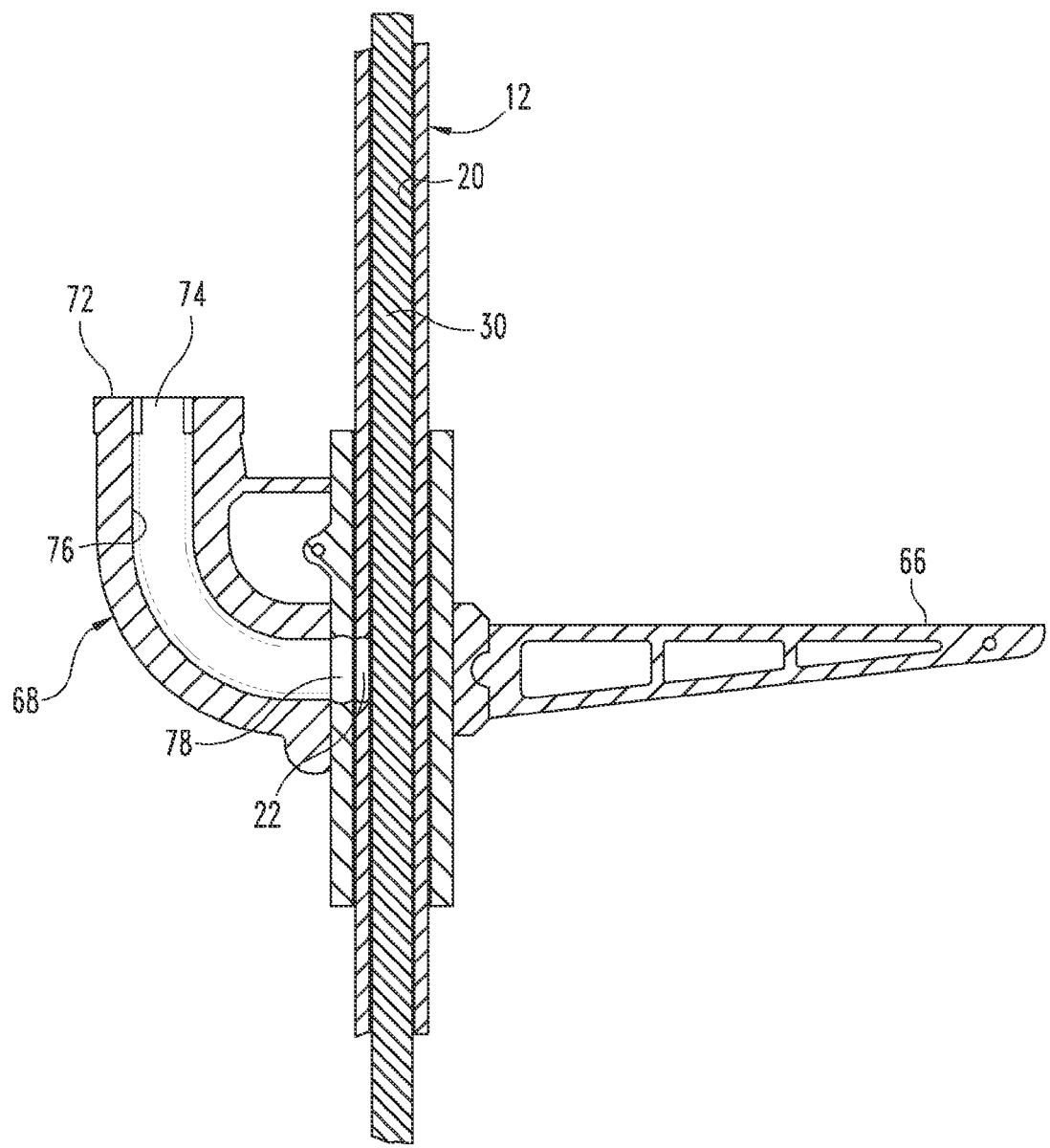
FIGS. 7A and 7B are section views of the apparatus illustrated in FIG. 1 taken along view line 7-7 in FIG. 2.
Figure 7B:
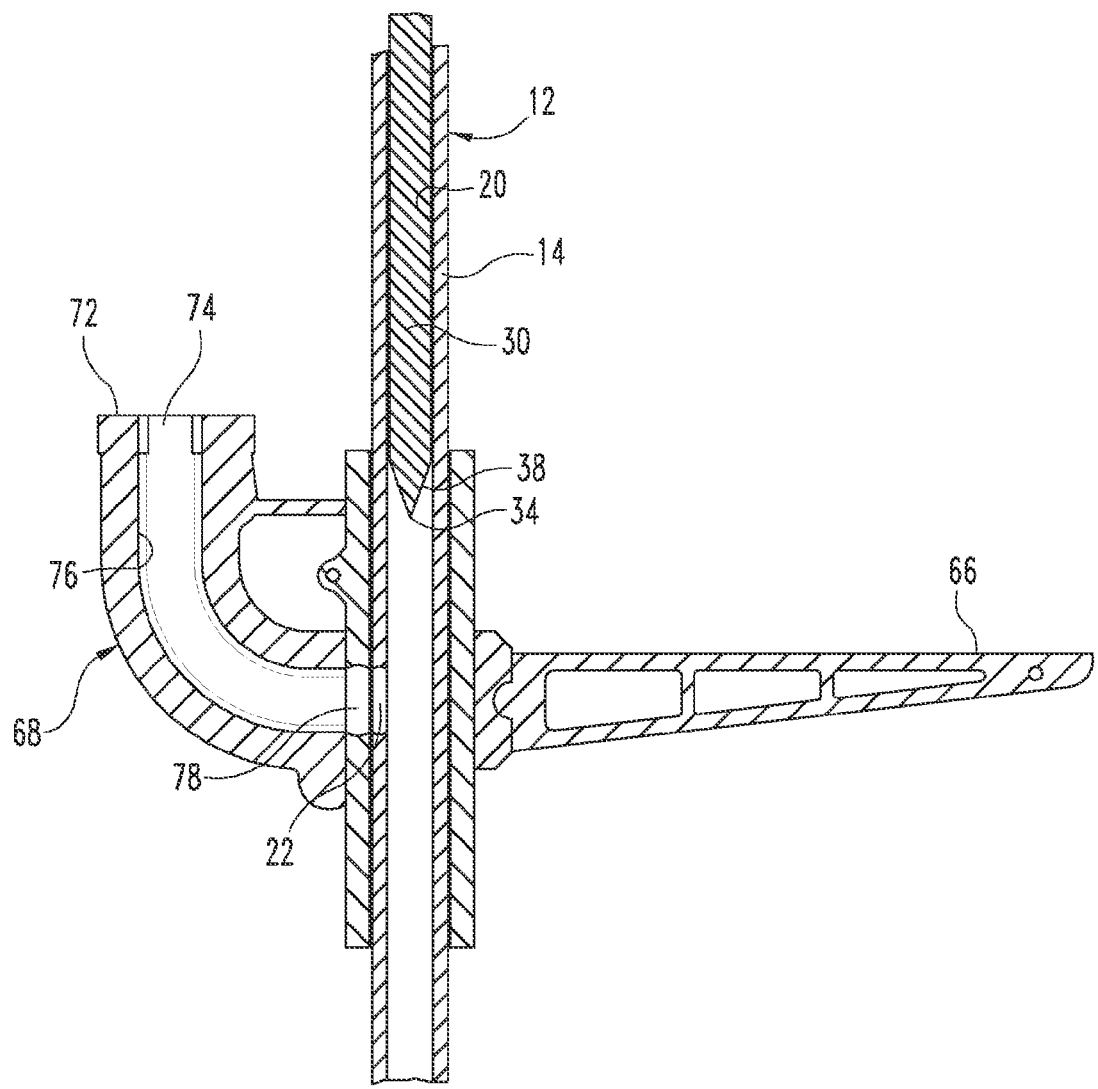

Turning now to FIG. 1, there is illustrated in plan view a non-limiting embodiment of an apparatus 10 configured to facilitate subterranean placement or positioning of one or more items. Apparatus 10 includes a first member 12 having an elongate body 14 extending along a longitudinal axis L between a proximal end 16 and an opposite distal end 18. In the illustrated form, elongate body 14 includes a chamfer or bevel that extends proximally from distal end 18 in order to help facilitate insertion of first member 12 at least partially into the ground if desired. It should be appreciated that non-illustrated forms in which such a chamfer or bevel is omitted are possible. First member 12 also includes an elongate bore 20 (FIGS. 7A and 7B) that extends between and opens through proximal end 16 and distal end 18 of elongate body 14. As illustrated in FIGS. 6, 7A and 7B, an opening 22 laterally extends through elongate body 14 and communicates with elongate bore 20. Opening 22 is positioned between proximal end 16 and distal end 18 and is generally configured to facilitate passage of one or more items into elongate bore 20, further details of which will be provided below. First member 12 also includes a pair of oppositely positioned handles 24, 26 positioned adjacent to proximal end 16. In the illustrated form, handles 24, 26 extend transversely to longitudinal axis L, and are generally configured to facilitate handling of apparatus 10 by an operator.

Figure 4:
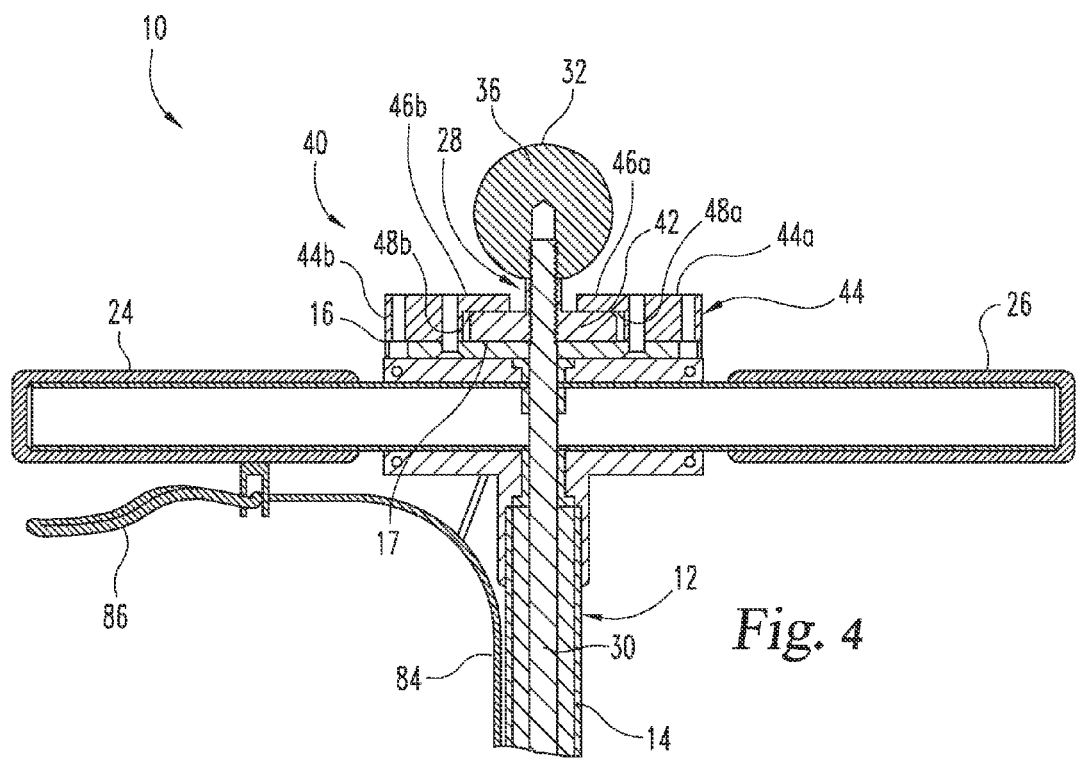
FIG. 4 is a section view of the proximal end portion of the apparatus illustrated in FIG. 1 taken along view line 4-4 in FIG. 2.

Apparatus 10 further includes a second member 28 having an elongate body 30 (FIGS. 4, 7A and 7B) extending between a proximal end 32 and a distal end 34. Proximal end 32 includes a round handle 36 configured to facilitate operator manipulation and control of second member 28 relative to first member 12. The leading portion of elongate body 30 includes a tapered section 38 positioned adjacent to distal end 34. Tapered section 38 is configured to facilitate formation of a hole as apparatus 10 is forced into the ground, and in other non-illustrated forms may include one or more cutting flutes or similar features to assist in formation of the hole. As illustrated in FIG. 1 for example, elongate body 30 extends through first member 12 such that tapered section 38 and distal end 34 are positioned distally of distal end 18 of first member 12. In this arrangement, tapered section 38 begins formation of a hole as apparatus 10 is initially forced into the ground and first member 12 is guided into the hole as apparatus 10 is progressively forced into the ground.

While not previously discussed, it should be understood that second member 28 is both rotatably and axially movable in elongate bore 20 along longitudinal axis L and relative to first member 12. However, apparatus 10 is configured to selectively restrain axial movement of second member 28 relative to first member 12 in order to maintain the relative positioning of first and second members 12, 28 that is shown in FIG. 1. Axial restraint of second member 28 in this manner prevents its proximal displacement relative to first member 12 as apparatus 10 is forced into the ground to form a hole. In this manner, tapered section 38 remains the leading portion of apparatus 10 as it is progressively forced into the ground and thereby assists in formation of the hole. In addition, it should be understood that maintaining the relative positioning of first and second members 12, 28 that is shown in FIG. 1 during hole formation prevents soil, rocks and other debris from plugging or otherwise clogging elongate bore 20. Similarly, once the hole has been formed, second member 28 may be axially withdrawn in a proximal direction such that a delivery pathway is provided by elongate bore 20 for placement of one or items in the formed hole, further details of which will be provided below.

Figure 2:
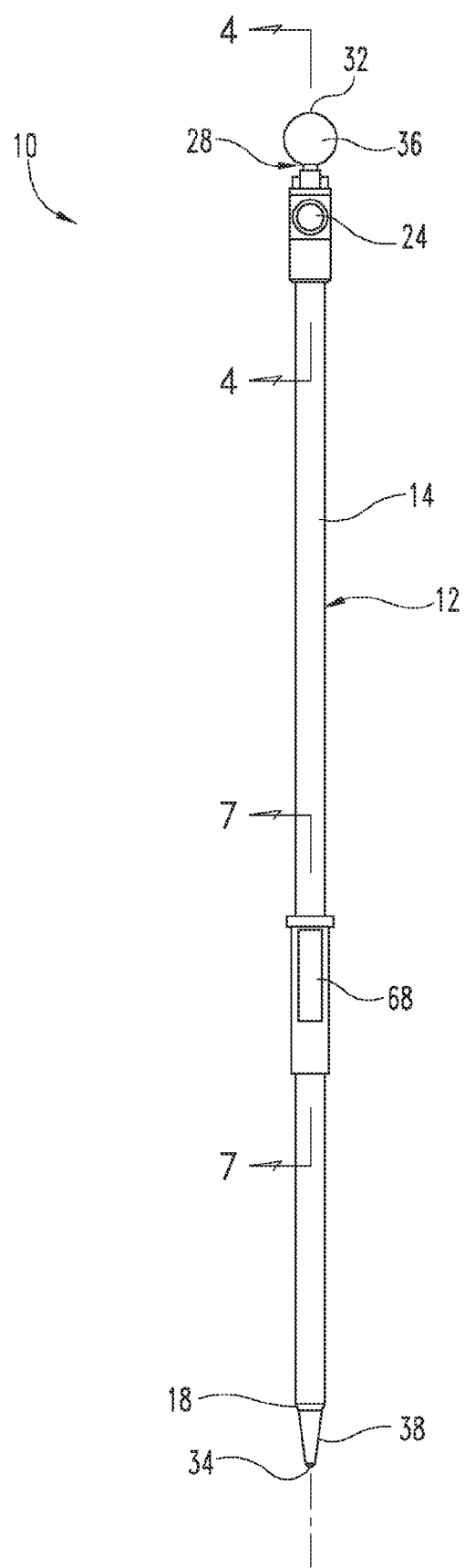
FIG. 2 is an alternative plan view of the apparatus illustrated in FIG. 1 in which some elements illustrated in FIG. 1 have been omitted.
Figure 3:
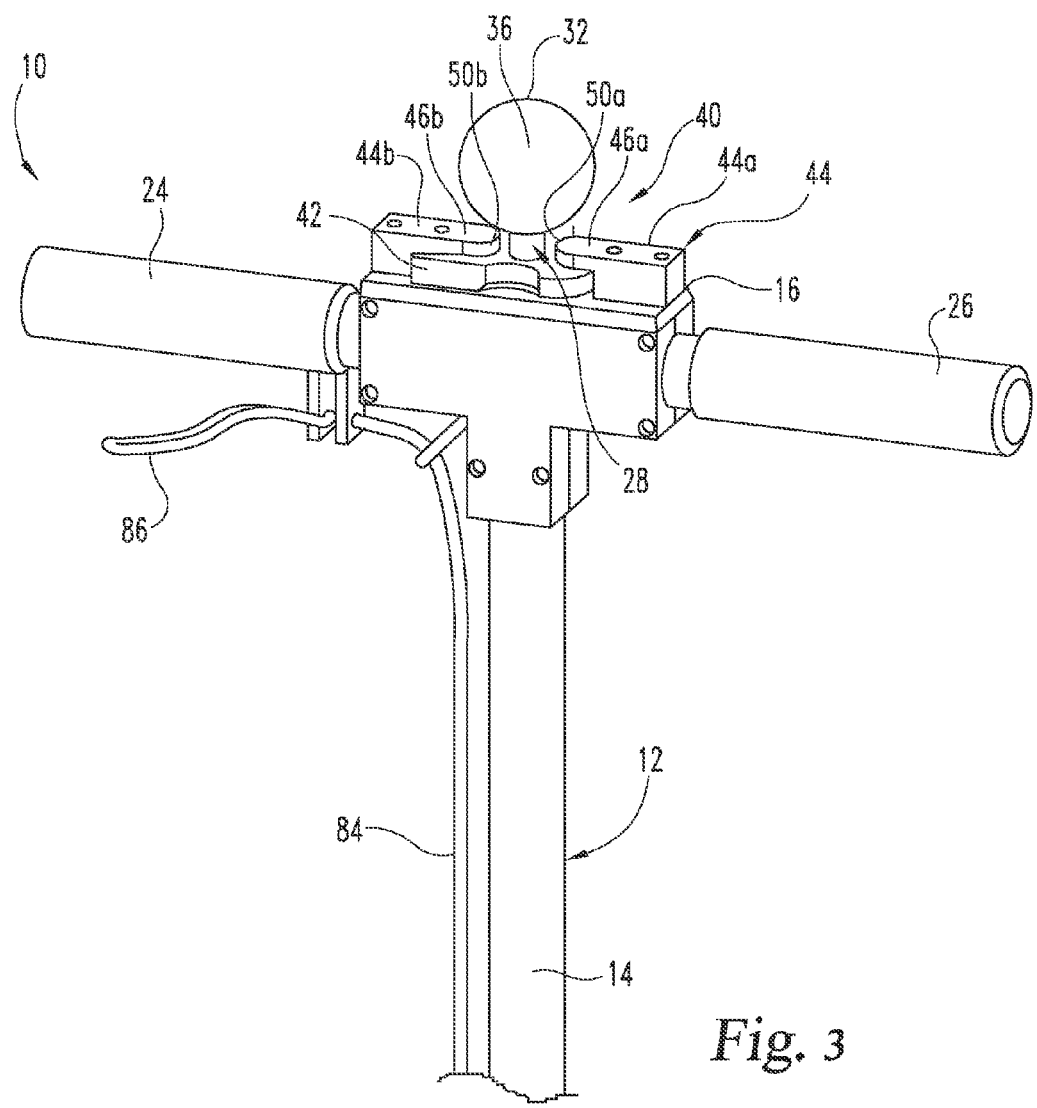
FIG. 3 is an enlarged, perspective view of a proximal end portion of the apparatus illustrated in FIG. 1.

In the illustrated form, apparatus 10 includes a locking arrangement 40 structured to restrain axial movement of second member 28 relative to first member 12 and otherwise maintain the relative positioning of first and second members 12, 28 that is shown in FIG. 1 where tapered section 38 extends distally beyond distal end 18 of first member 12. Further details regarding locking arrangement 40 will now be provided in connection with FIG. 3, which is an enlarged perspective view of the proximal end portion of apparatus 10, and FIG. 4, which is a section view of the proximal end portion of apparatus 10 taken along view line 4-4 of FIG. 2. Locking arrangement 40 includes a latching member 42 which is positioned on second member 28, and a flange 44 which is positioned on first member 12. Flange 44 is generally defined by a pair of portions 44a, 44b which are oppositely positioned and laterally spaced from one another on a proximal facing surface 17 of first member 12. Portion 44a includes an overhung section 46a which defines a space 48a between portion 44a and proximal facing surface 17. Overhung section 46a also includes a convexly rounded portion 50a facing toward portion 44b. Portion 44b includes an overhung section 46b which defines a space 48b between portion 44b and proximal facing surface 17. Overhung section 46b also includes a convexly rounded portion 50b facing toward portion 44a.

Figure 5:
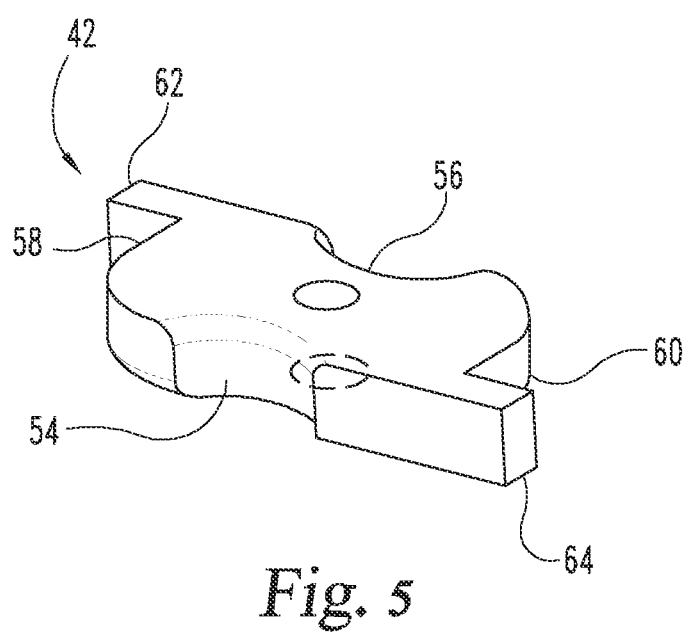
FIG. 5 is a perspective view of a latching member included on the proximal end portion of the apparatus illustrated in FIG. 1.

As best seen in FIG. 5 for example, latching member 42 includes a concave portion 54 positioned opposite of a concave portion 56. Concave portions 58, 60 are positioned between end portions 58 and 60 which include stops 62 and 64, respectively. Turning again to FIGS. 3 and 4, end portions 58, 60 of latching member 42 are sized and structured to fit into spaces 48a, 48b formed by portions 44a, 44b, respectively, of flange 44. In addition, when second member 28 is rotated to the position illustrated in FIGS. 3 and 4, stops 62 and 64 come into contact with portions 44a and 44b of flange 44 in order to prevent continued rotation of second member 28 and also provide a tactile indication to an operator of apparatus 10 that end portions 58, 60 of latching member 42 are positioned in spaces 48a, 48b. When so positioned, flange 44 prevents axial movement of first and second members 12, 28 relative to one another and also maintains the relative positioning therebetween that is illustrated in FIG. 1 for example. When axial restraint of second member 28 relative to first member 12 is no longer desired, second member 28 can be rotated relative to first member 12 to bring concave portions 58, 60 of latching member 42 into alignment with correspondingly sized and shaped convexly rounded portions 50a, 50b of portions 44a, 44b. Once aligned in this manner, second member 28 may be distally and axially displaced relative to first member 12.

In the illustrated form, axial movement of second member 28 relative to first member 12 is proximally and distally restrained when latching member 42 is engaged with flange 44. In alternative forms, it is contemplated that apparatus 10 could be structured such that second member 28 is provided with a range of proximal and distal axial movement relative to first member 12 when latching member is engaged with or otherwise rotationally positioned to be engaged with flange 44. For example, in one such form spaces 48a, 48b could have a dimension in a proximal-distal direction that is greater than the thickness of latching member 42. In this form, the positioning of latching member 42 and flange 44 may be such that tapered section 38 and distal end 34 remain positioned distally of distal end 18 of first member 12 when second member 28 is restrained at its proximal most position by flange 44. It should also be understood that other arrangements for axially restraining second member 28 relative to first member 12 are possible. For example, in addition or as an alternative to locking arrangement 40, apparatus could be structured to include a pin that extends through first member 12 and bears against or extends at least partially into second member 28 in order to restrain axial movement therebetween. As another example, one or both of first member 12 and second member 28 could be provided with a spring loaded detent or other projection that fits into a corresponding recess or hole in the other of first member 12 and second member 28 in order to restrain axial movement therebetween. The foregoing examples are non-limiting, and it should be appreciated that others are possible and contemplated.

Referring back to FIG. 1, apparatus 10 also includes a platform 66 that extends transversely from a first side of first member 12. Platform 66 is generally configured to facilitate placement of an operator's foot thereon so force may be applied thereto when apparatus 10 is forced toward the ground during formation of the hole, and it may likewise include a roughened upper surface or be provided with other gripping features. While the illustrated form of apparatus 10 only includes one platform 66, it should be appreciated that forms in which a pair of platforms 66 are positioned opposite of one another are possible. A mounting portion 68 extends transversely from first member 12 opposite of platform 66 and is configured to engage with a dispensing unit 70. It should be understood that platform 66 and mounting portion 68 may act as a stop which limits the depth to which apparatus 10 may be inserted into the ground. In one form, the distance between distal end 34 of second member 28 and platform 66 and mounting portion 68, and hence the depth to which apparatus 10 may be inserted into the ground, is in the range of 1 to 18 inches. In yet another form, the distance between distal end 34 of second member 28 and platform 66 and mounting portion 68 is in the range of 2 to 16 inches. In still another form, the distance between distal end 34 of second member 28 and platform 66 and mounting portion 68 is in the range of 3 to 14 inches. In yet another form, the distance between distal end 34 of second member 28 and platform 66 and mounting portion 68 is in the range of 4 to 12 inches. It should be understood however that alternative values for the distance between distal end 34 of second member 28 and platform 66 and mounting portion 68 are possible. In addition, in one non-illustrated form, apparatus 10 may be provided with an adjustable depth stop that is positioned distally of platform 66 and mounting portion 68 and will control the depth to which apparatus 10 may be inserted into the ground.

As illustrated in FIGS. 7A and 7B, mounting portion 68 includes a mounting surface 72 on which dispensing unit 70 may be positioned. A first opening 74 extends through surface 72 and communicates with passageway 76 formed in mounting portion 68. Opposite first opening 74, mounting portion 68 includes a second opening 78 positioned in communication with passageway 76 and opening 22 of first member 12. Similarly, it should be understood that first opening 74, passageway 76, second opening 78 and opening 22 are arranged such that any items passed through first opening 74 may be directed into elongate bore 20. When distal end 34 of second member 28 is positioned distally of opening 22 as shown in FIG. 7A, e.g. when first and second members 12, 28 are axially restrained relative to one another during hole formation, elongate body 30 will obstruct opening 22 and prevent items from entering into elongate bore 20. However, once second member 28 is distally displaced relative to first member 12 and distal end 34 of second member 28 is positioned proximally of opening 22 as illustrated in FIG. 7B for example, opening 22 will no longer be obstructed by elongate body 30 and items may enter elongate bore 20 and be guided into a hole formed by apparatus 10.

Dispensing unit 70 is positioned on mounting surface 72 and engaged with mounting portion 68. In one form, dispensing unit 70 may be releasably engaged with mounting portion 68 utilizing, for example, a threaded arrangement or a bayonet lock, although it should understood that other arrangements could be used. Dispensing unit 70 includes a container 88 configured to hold a plurality of items that may be subsequently dispensed into elongate bore 20. A removable cover 82 is positioned on the proximal end of dispensing unit 70 and facilitates loading of container 88. Dispensing unit 70 also includes a release member 80 which is configured to selectively control the release of the items of container 88. Release member 80 is coupled by cable 84 with an actuator in the form of a spring loaded or otherwise biased lever 86. In one form, release member 80 may generally cover or obstruct an opening on the distal end of container 88 in order to prevent release of its contents unless and until lever 86 is actuated. Similarly, upon actuation of lever 86, release member 80 may be laterally displaced such that the opening on the distal end of container 88 is no longer obstructed and one or more of the items stored in container 88 may pass through opening 74 of mounting portion 68 and be guided toward elongate bore 20. In other forms, it is contemplated that release member 80 may be specifically configured such that only a single item stored in container 88 will be released for each time lever 86 is actuated. For example, in one such form dispensing unit 70 may be in the form of a suitably configured rotary dispenser. While not previously discussed, it should be appreciated that an operator of apparatus 10 may control the timing of release of items from container 88 until after a hole has been formed by apparatus 10 and elongate bore 20 and opening 22 are not obstructed by second member 20. In addition, depending on the specific configuration of dispensing unit 70, an operator of apparatus 10 may generally or specifically control the number of items which are released from container 88 and deposited into a hole formed by apparatus 10.

Forms in which one or both of mounting portion 68 and dispensing unit 70 are absent or alternatively configured are also contemplated. For example, in one non-illustrated form dispensing unit 70 may be omitted and an item to be deposited in a hole formed by apparatus 10 may be directly placed through first opening 72 of mounting portion 68. In another non-illustrated form, a guide tube or other pathway may extend proximally from mounting portion 68 to a location adjacent to one or both of handles 24, 26 and provide a delivery pathway that extends distally into communication with elongate bore 20. In this form, dispensing unit 70 may be omitted and items can be placed directly into the guide tube at the location adjacent to one or both of handles 24, 26, or dispensing unit 70 may be mounted on the guide tube at the location adjacent to one or both of handles 24, 26. In still another form, mounting portion 68 may be omitted and items may be placed directly through opening 22 into elongate bore 20. In yet another form, mounting portion 68 and opening 22 may be omitted and elongate bore 20 provides a delivery pathway from proximal end 16 to the hole formed by apparatus 10 when second member 28 is axially withdrawn and removed from first member 12. In addition, it is further contemplated that dispensing unit 70 may be provided with an electro-mechanical or other suitable configuration in lieu of the use of lever 86 as an actuator. In one non-limiting form for example, a controller may be positioned on one of handles 24, 26 and communicate with dispensing unit 70 to provide commands for releasing items from container 88. Notwithstanding the foregoing, it should be appreciated that additional configurations are contemplated and possible for one or both of mounting portion 68 and dispensing unit 70.

Further details regarding one non-limiting technique for using apparatus 10 to form a hole and subsequently place one or more items therein will now be provided. When the relative axial positioning of first and second members 12, 28 is restrained and tapered section 38 extends distally from distal end 18 of first member 12, an operator of apparatus 10 may bring distal end 34 of second member 28 into contact with the ground. A downward force may then be applied to apparatus 10 to force the leading end of apparatus into the ground and form a hole with one or both of tapered section 38 of second member 28 and a portion of first member 12. Once the hole has been formed to a desired depth, axial restraint of second member 28 relative to first member 12 may be released and second member 28 may be axially moved in a proximal direction relative to first member 12 until elongate body 30 no longer obstructs opening 22. The positioning of first member 12 may be maintained in order to keep a portion of first member 12 in the hole or otherwise have elongate bore 20 axially aligned with the hole. Once second member 28 is positioned in the manner described above, one or more items may be released from dispensing unit 70 into elongate bore 20 and then guided thereby into the hole formed by apparatus 10. After the desired number of items has been placed into the hole formed by apparatus 10, apparatus 10 may be removed from the hole and the hole may be optionally covered by soil or other fill material. This technique may be repeated any number of times, and optionally in a desired pattern or array, in a given area until the desired number of items has been subterraneously placed.

While not previously discussed, it should be appreciated that apparatus 10 may be used to subterraneously place or position a variety of different items. In one form, these items may include agricultural products such as seeds or delivery vehicles that include one or more fertilizers or pesticides or combinations of these materials. As used herein, the term "pesticide" is intended to encompass herbicides, fungicides, insecticides and bactericides. Similarly, depending on the particular form of the pesticide composition, pests that can be targeted by the disclosed delivery vehicles include insects, plant pathogens, weeds, molluscs, nematodes, and microbes. It should be appreciated however that the foregoing are merely non-limiting examples.

In one aspect, the delivery vehicle is a capsule configured to resist release of a pesticide composition before application of the capsule at a locus where pest control is desired. The capsule is further configured to degrade following application at the locus where pest control is desired to facilitate release of the pesticide composition. In certain forms, the capsule is also configured to control various aspects of the release of the pesticide composition, including for example its time and rate of release. In one particular but non-limiting form, the capsule includes a shell wall including a gelatin material and encapsulating a pesticide composition that includes a fumigant such as 1,3-dichloropropene. Further details regarding forms of this and other types of capsules that can be subterraneously placed or positioned with apparatus 10 are found in U.S. Provisional Patent Application No. 61/640,392, the contents of which are incorporated herein by reference in their entirety. In view of the foregoing, in one non-limiting embodiment apparatus 10 includes a plurality of capsules that include a pesticide composition contained in dispensing unit 70, although forms in which other types of items or capsules or stored in dispensing unit 70 are possible.

Other examples of pesticides that could be included, either singularly or in combination, in capsules that can be subterraneously placed or positioned by apparatus 10 include insecticides such as antibiotic insecticides, macrocyclic lactone insecticides (for example, avermectin insecticides, milbemycin insecticides, and spinosyn insecticides), arsenical insecticides, botanical insecticides, carbamate insecticides (for example, benzofuranyl methylcarbamate insecticides, dimethylcarbamate insecticides, oxime carbamate insecticides, and phenyl methylcarbamate insecticides), diamide insecticides, desiccant insecticides, dinitrophenol insecticides, fluorine insecticides, formamidine insecticides, inorganic insecticides, insect growth regulators (for example, chitin synthesis inhibitors, juvenile hormone mimics, juvenile hormones, moulting hormone agonists, moulting hormones, moulting inhibitors, precocenes, and other unclassified insect growth regulators), nereistoxin analogue insecticides, nicotinoid insecticides (for example, nitroguanidine insecticides, nitromethylene insecticides, and pyridylmethylamine insecticides), organochlorine insecticides, organophosphorus insecticides, oxadiazine insecticides, oxadiazolone insecticides, phthalimide insecticides, pyrazole insecticides, pyrethroid insecticides, pyrimidinamine insecticides, pyrrole insecticides, tetramic acid insecticides, tetronic acid insecticides, thiazole insecticides, thiazolidine insecticides, thiourea insecticides, urea insecticides, as well as, other unclassified insecticides.

More particular examples of insecticides include, but are not limited to, labamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-endosulfan, amidithion, aminocarb, amiton, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bioresmethrin, bistrifluron, borax, boric acid, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chlorantraniliprole, chlorbicyclen, chlordane, chlordecone, chlordimeform, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinoprop, dinosam, dinotefuran, diofenolan, dioxabenzofos, dioxacarb, dioxathion, disulfoton, dithicrofos, d-limonene, DNOC, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate-methyl, ethoprophos, ethyl formate, ethyl-DDD, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formothion, formparanate, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methylchloroform, methylene chloride, metofluthrin, metolcarb, metoxadiazone, mevinphos, mexacarbate, milbemectin, milbemycin oxime, mipafox, mirex, monocrotophos, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluthrin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulfluramid, sulfotep, sulfuryl fluoride, sulprofos, tau-fluvalinate, tazimcarb, TDE, tebufenozide, tebufenpyrad, tebupirimfos, tefluben-zuron, tefluthrin, temephos, TEPP, terallethrin, terbufos, tetrachloroethane, tetrachlorvinphos, tetramethrin, theta-cypermethrin, thiacloprid, thiamethoxam, thicrofos, thiocarboxime, thiocyclam, thiodicarb, thiofanox, thiometon, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and α-ecdysone.

For more information consult "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council.

In forms in which apparatus 10 is used to subterraneously place or position a capsule that includes a pesticide, the locus to which the capsules may be applied can be any locus inhabited by a pest including, for example, areas having vegetable crops, fruit and nut trees, grape vines, grasses, and ornamental plants, just to provide a few non-limiting possibilities. Controlling pests generally means that pest populations, activity, or both, are reduced in a locus. This can come about when: pest populations are repulsed from a locus; when pests are incapacitated in or around a locus; or pests are exterminated, in whole or in part, in or around a locus. Of course a combination of these results can occur.

While the invention has been illustrated and described in detail in the drawings and foregoing description, the same is to be considered as illustrative and not restrictive in character, it being understood that only certain embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. An apparatus, comprising:
   a first member including a first elongate body extending along a longitudinal axis between a proximal end and a distal end, the first elongate body including an elongate bore extending between a first opening at the proximal end and a second opening at the distal end;
   a second member positionable in the elongate bore, the second member including a second elongate body extending along a longitudinal axis between a proximal end and a distal end; and
   a locking arrangement including a first portion positioned on the first member proximally of the first opening and a second portion positioned on the second member;
   wherein the second member is rotatable relative to the first member about the longitudinal axis between a first position where the first and second portions are engaged and the second portion bears against the first member proximally of the first opening to prevent distal movement of the second member relative to the first member and a second position where the first and second portions are disengaged.

2. The apparatus of claim 1, wherein axial movement of the second member along the longitudinal axis is prevented when the second member is in the first position and the first and second portions of the locking arrangement are engaged.

3. The apparatus of claim 2, wherein the second portion of the locking arrangement includes a proximal surface positioned opposite of a distal surface and a first side positioned opposite of a second side, the first and second sides each extending between the proximal and distal surfaces and including an arcuate portion inwardly extending toward the other side.

4. The apparatus of claim 3, wherein the arcuate portions each include a radiused profile adjacent the distal surface.

5. The apparatus of claim 3, wherein the first side further includes a convex portion and a linear portion and the arcuate portion of the first side is positioned between the convex portion and the linear portion.

6. The apparatus of claim 5, wherein the convex portion includes a radiused profile adjacent the proximal surface.

* * * * *